United States Patent [19]
Domb et al.

[11] Patent Number: 6,011,008
[45] Date of Patent: *Jan. 4, 2000

[54] CONJUGATES OF BIOLOGICALLY ACTIVE SUBSTANCES

[75] Inventors: Abraham J. Domb, Efrat; Shimon Benita, Mevasseret Zion; Itzhack Polacheck, Jerusalem; Galina Linden, Bat Yam, all of Israel

[73] Assignee: Yissum Research Developement Company Of The Hebrew University Of Jerusalem, Jerusalem, Israel

[*] Notice: This patent is subject to a terminal disclaimer.

[21] Appl. No.: 09/090,587

[22] Filed: Jun. 4, 1998

Related U.S. Application Data

[63] Continuation of application No. 08/780,677, Jan. 8, 1997, abandoned.

[51] Int. Cl.$^7$ .......................... A61K 37/02; A61K 37/36; C07K 13/00
[52] U.S. Cl. ............................... 514/8; 514/25; 530/395; 536/6.4; 536/18.6; 536/123.1
[58] Field of Search .................... 514/25, 8, 21; 536/6.5, 123.1, 18.6; 530/395

[56] References Cited

U.S. PATENT DOCUMENTS

| | | |
|---|---|---|
| 4,446,316 | 5/1984 | Chazov et al. . |
| 4,587,122 | 5/1986 | Kagitani et al. . |
| 4,707,471 | 11/1987 | Laum . |
| 5,059,685 | 10/1991 | Conti . |
| 5,177,059 | 1/1993 | Handley et al. . |
| 5,332,567 | 7/1994 | Goldenberg . |
| 5,393,737 | 2/1995 | Mayers et al. ............................ 514/12 |
| 5,567,685 | 10/1996 | Linden et al. ............................ 514/31 |

FOREIGN PATENT DOCUMENTS

| | | |
|---|---|---|
| 0 466 038 | 1/1992 | European Pat. Off. . |
| 0 574 638 | 12/1993 | European Pat. Off. . |
| 2 342 740 | 3/1977 | France . |
| 2 640 141 | 6/1990 | France . |
| 87 778 | 11/1972 | Germany . |
| 3032606 | 1/1984 | Germany . |
| 61-64701 | of 1986 | Japan . |
| 809105 | 2/1959 | United Kingdom . |
| 844289 | 9/1960 | United Kingdom . |
| 1 509 587 | 5/1978 | United Kingdom . |
| 978170 | 12/1994 | United Kingdom . |
| WO 90/15628 | 12/1990 | WIPO . |
| 93/25239 | 12/1993 | WIPO . |
| 9512620 | 5/1995 | WIPO . |

OTHER PUBLICATIONS

R. Mehta et al., "Liposomal Amphotericin B is Toxic to Fungal Cells But Not to Mammalian Cells", BBA Report, 1984, pp. 230–234.

M. Maddux et al., "Review of Complicatioans of Amphotericin–B Therapy: Recommendations for Preventtion and Management", Drug Intelligence and Clinical Pharmacy, vol. 14, Mar. '80, pp. 177–181.

R. Mehta et al., "Formulation Toxicity, and Antifungal Activity in Vitro of Liposome–Encapsulated Nystatin as Therapeutic Agent for Systemic Candidasis", Antimicrob. Agents Chemero., Dec. 1987, pp. 1897–1900, vol. 31, No. 12.

M. DeGregorio et al., "Candida Infections in Patients with Acute Leukemia: Ineffectiveness of Nystatin Prophylaxis and Relationship Between Oropharyngeal and Systemic Candidiasis", Amer. Cancer Soc., Dec, 1982, vol. 50, pp. 2780–2784.

K.P. Khomyakov et al., "Synthesis of Polymeric Drugs from Dextrain Derivative Synthesis of Polymeric drugs", pp. 1145–1151.

L. Polacheck et al., "Activity of Compound G2 Isolated form Alfalfa Roots against Medically Important Yeasts", Antimicorbial Agents Chemo., Aug. '86, vol. 30, No. 2, pp. 290–294.

G. Lindenbaum et al., J. Khim–Pharm. 1977, vol. 11, No. 6, pp. 80–83.

G. Lindebaum et al., Prikl. Biochim. Mikrobiol. 1982, vol. 18, No. 2, pp. 212–220 (Russ).

G. Michael, "Nystatin", Analytical Profiles of Drugs Substances, No. 6, pp. 341–421, 1977.

Bucklin et al., Therapeutic Efficacy of Polymyxin B–Dextran 70 Conjugate in Experimental Model Endotoxemia, Jul. 1995, pp. 1462–1466.

S.W. Shalaby, ed. Biomedical polymers–Designed to degrade systems, Carl Hanser, Munich, 1994. pp. 223.

Larson, C., 1990, in Dextran Prodrugs. Physico–chemical and chemical aspects in relations to in vivo properties, Arhus. Odense. 233 p.

Levy–Shaffer, F., Berstein, A., et al., 1982, Cancer Treat. Rep., 66, 107–144.

Bornstein, A., Hurwitz, E., et al., 1978, J. Nat. Cancer Inst., 60., 379–384.

Law, S., Lo, W., & Teh. G., 1988, Drug. Dev. Ind. Pharm., 14, 143–153.

Rogovin, Z., Vymic, A., Khomyakov, K. et al., 1972, Vysokomol. Soed., 7, 1035–1040.

(List continued on next page.)

*Primary Examiner*—Elli Peselev
*Attorney, Agent, or Firm*—Helfgott & Karas, P.C.

[57] ABSTRACT

A method for producing a water-soluble polysaccharide conjugate of an oxidation-sensitive substance is described. The method comprises the following steps: (a) activating the polysaccharide to a dialdehyde by periodate oxidation; (b) purifying the dialdehyde from interfering anions and by-products; and (c) coupling the substance to the purified dialdehyde by Schiff base formation to form the conjugate. Optionally, the conjugate of step (c) is reduced to an amine conjugate by a reducing substance. The product conjugate may then be further purified from various reaction byproducts. The disclosed method results in the substance substantially retaining its biological activity. Also described are imine and amine polysaccharide conjugates of various drugs and polypeptides.

32 Claims, 2 Drawing Sheets

OTHER PUBLICATIONS

Hurwitz, E., et al., 1980, J. Appl. Biochem., 2, 25–35.

Stewart, J.M., Young, J.D., Solid Peptide Synthesis, Rockford, ILL., USA, Price Chem. Company, 1984, pp. 115.

Mocanu et al., Macromolecular Drug Conjugates II. Metronidaz Dextran Prodrugs, Oct. 1993, pp. 383–392.

Cera et al., Anthracycline Antiotics Supported on Water Soluable Polysaccharides: Synthesis and Psysicochemical characterization, Apr. 1988, pp. 66–74.

Manable et al., Production of a Monoclonal Antibody–Mitomycin Conjugate, Utilizing Dextran T–40, and its Biological Activit Mar. 1994, pp. 289–291.

CONJUGATES OF BIOLOGICALLY ACTIVE SUBSTANCES

This is a continuation of U.S. Ser. No. 08/780,677, filed Jan. 8, 1997, now abandoned.

FIELD OF THE INVENTION

The present invention relates to a method for preparing water-soluble polysaccharide conjugates of biologically active substances which are oxidation sensitive. The invention also relates to conjugates prepared by the method and pharmaceutical compositions comprising them.

BACKGROUND OF THE INVENTION

Reference is made in this specification, by way of superscripted numerals, to a number of publications listed at the end of the disclosure.

Numerous drugs exist which cannot be administered systemically due to their water insolubility, toxicity and/or instability. Many of these drugs are also sensitive to oxidation, including but not limited to, 5-amino salicylic acid, aminoglucoside antibiotics, flucytosine, pyrimethamine, sulfadiazine, dapsone, trimethoprim, mitomycins, methotrexate, doxorubicin, daunorubicin and polymyxin B. Peptides containing oxidation sensitive amino acids such as cysteine, methionine, tyrosine, histidine and tryptophan [1] and amino acid ester derivatives of hydroxyl containing oxidizable drugs which contain a primary amine are also sensitive to oxidation. One solution for stabilizing such drugs is to conjugate them to a carrier.

Water soluble, oxidized polysaccharides such as, for example, dextrans are considered to be one of the most attractive drug carrier candidates [2]. Dialdehydedextran (DAD), the main product of the oxidation reaction of periodate with dextran, has been proposed as a stabilizer for enzymes and drugs, including antibiotics [3-8]. However, oxidation-sensitive drugs such as those listed above lose a major portion of their biological activity following conjugation.

GB 978,170 describes a process for the preparation of water-soluble imine derivatives of polyene antibiotics, in which a polysaccharide is oxidized to a polydialdehyde prior to being reacted with the polyene. Among the conjugates described in this patent are pimaricin-dextran and Nystatin-corn starch. No amine conjugates are described in the British patent.

In experiments carried out by the applicant of the present application, and described in Example XI below, it was found that although a Nystatin-dextran conjugate prepared according to the process described in the above patent is water-soluble, it has very low stability and activity, and is susceptible to drastic degradation of the polymer and inactivation of the conjugated drug. It is believed that this is due to the fact that the oxidized polymer is not purified from excess oxidizing agent prior to conjugation, thus resulting in the polyene undergoing oxidation. This purification was found to be essential for the stability, efficacy and lack of toxicity of the conjugated drug, as will be further described below.

BRIEF SUMMARY OF THE INVENTION

It is an object of the present invention to provide a method for the preparation of water-soluble oxidation sensitive substances which are also suitable for parenteral administration.

It is a further object of the present invention to provide a pharmaceutical composition comprising a water-soluble conjugate of an oxidation sensitive substance which is suitable for parenteral administration as well as for topical and oral application.

The present invention provides a solution to the problem of preparing water soluble conjugates of oxidation sensitive substances which, until now, have become oxidized during the conjugation process, thus losing a significant portion of their activity. The invention provides water soluble conjugates whose biological activity is comparable to the activity of the free substance, with the added advantage of water solubility.

According to one aspect of the present invention, there is provided a method for producing a water-soluble polysaccharide conjugate of an unoxidized, oxidation sensitive substance comprising:

(a) activating the polysaccharide to a dialdehyde by periodate oxidation;

(b) purifying the dialdehyde from interfering anions and by-products; and (c) coupling the substance to the purified dialdehyde by Schiff base formation to form the conjugate.

According to a second aspect of the present invention, the conjugate product of step (c) above is reduced to an amine conjugate by a reducing substance.

The conjugate obtained after step (c) or after reduction may be purified from undesired byproducts and unreacted reactants to yield a purified conjugate. Purification is particularly required when the conjugate is intended for therapeutic use.

According to another aspect of the present invention, there is provided a water-soluble conjugate of a polysaccharide and an unoxidized, oxidation-sensitive substance. The substance may be conjugated to the polysaccharide via either an imine or amine bond.

According to yet another aspect of the present invention, there is provided a pharmaceutical composition for use in the treatment of various physiological disorders comprising the conjugate of the invention as the active ingredient. Examples of such disorders include cancer, microbial infection and inflammation.

In a preferred embodiment of the present invention, the substance is selected from the group consisting of low molecular weight drugs and amine drug derivatives, and low molecular weight polypeptides and polypeptide analogs. Polyene antibiotics are excluded from the substances included in the conjugates of the invention.

The term "low molecular weight drug" in this specification refers to a drug having a molecular weight of less than 6000 Daltons. Examples of such drugs include, but are not limited to 5-amino salicylic acid, aminoglucoside antibiotics, flucytosine, pyrimethamine, sulfadiazine, dapsone, trimethoprim, mitomycins, methotrexate, doxorubicin, daunorubicin and polymyxin B.

The term "amine drug derivatives" refers to oligo-peptyl esters of hydroxyl containing drugs which contain a primary amine. The oligopeptide chain can comprise identical or different amino acids and will usually contain 10 amino acids or less. Examples of such derivatives include, but are not limited to, alanyl-Taxol, triglycyl-Taxol, alanyl-glycyl-dexamethasone, glycyl-dexamethasone and alanyl-dexamethasone.

The term "low molecular weight polypeptide" in this specification refers to a peptide or polypeptide having a molecular weight of less than about 6000 Daltons. Oxidation sensitive polypeptides are those comprising one or more oxidizable amino acids such as cysteine, methionine, tyrosine, histidine and tryptophan. Examples of such polypeptides include, but are not limited to, luteinizing hormone releasing hormone (LHRH), bradykinin, vasopressin, oxytocin, somatostatin, thyrotropin releasing factor (TRF), gonadotropin releasing hormone (GnRH), insulin and calcitonine.

The term "polypeptide analogs" in this specification refers to chemical modifications of bioactive peptides including cyclic derivatives, N-alkyl derivatives, derivatives in which fatty acids are attached to the amino acid terminals or along the peptide chain, and reverse amino acid derivatives.

The polysaccharide of the invention may be natural or synthetic and may be either branched or linear. An example of a linear polysaccharide is dextran. Examples of branched natural or semisynthetic polysaccharides are arabinogalactan (AG) and branched dextran, respectively. The molecular weight of the polysaccharide useful in accordance with the invention will generally be in the range of about 5000–75,000 Dalton.

The reaction of periodate with a polysaccharide (structure A, FIG. 1) leading to an oxidized polysaccharide (OP—structure B) is well-studied. The separation of the activated polymer from the interfering anions (periodate, iodate and formate) of the reaction mixture may be achieved, for example, by applying the reaction mixture to a column filled with a strongly basic anion-exchanger in the acetate form. This process of purification is fast and provides a high yield of the purified OP at the initial concentration, the anion-exchanger being easily regenerated afterwards.

The OP may then be reacted with the amino group of a biologically active substance (in the example of FIG. 1—doxorubicin) to form a Schiff base (structure C). The imine conjugate is useful for therapeutic applications where it is desired that the conjugate be hydrolyzed within a cell to release the active substance. Optionally, the Schiff base bond may be converted into a stable amine bond by a reducing substance, preferably sodium or potassium borohydride (structure D). Such a bond is unlikely to be easily hydrolyzed in the body. It is to be understood that other reducing substances, such as $NaHSO_3$ can also be used.

The conjugate may then be separated from the salts, low molecular weight polymer fractions and traces of unbound water-soluble drug by dialysis, followed by centrifugation and lyophilization.

The conjugates do not contribute markedly to an increase in osmotic pressure, notwithstanding their high molecular weight. Therefore for the preparation of an parenteral solution, e.g. an intravenous composition, the lyophilized conjugate is simply dissolved in saline and sterilized by filtration or autoclaving.

If it is desired to prepare compositions in the form of eye or ear drops, appropriate preservatives such as parahydroxybenzoate ester derivatives (methyl, propyl, butyl) may be added to the composition.

BRIEF DESCRIPTION OF THE DRAWINGS

The present invention will be better understood from the following detailed description of preferred embodiments, taken in conjunction with the following drawings in which.

DETAILED DESCRIPTION OF PREFERRED EMBODIMENTS

METHODS

1. Chromatography

Figure 1:
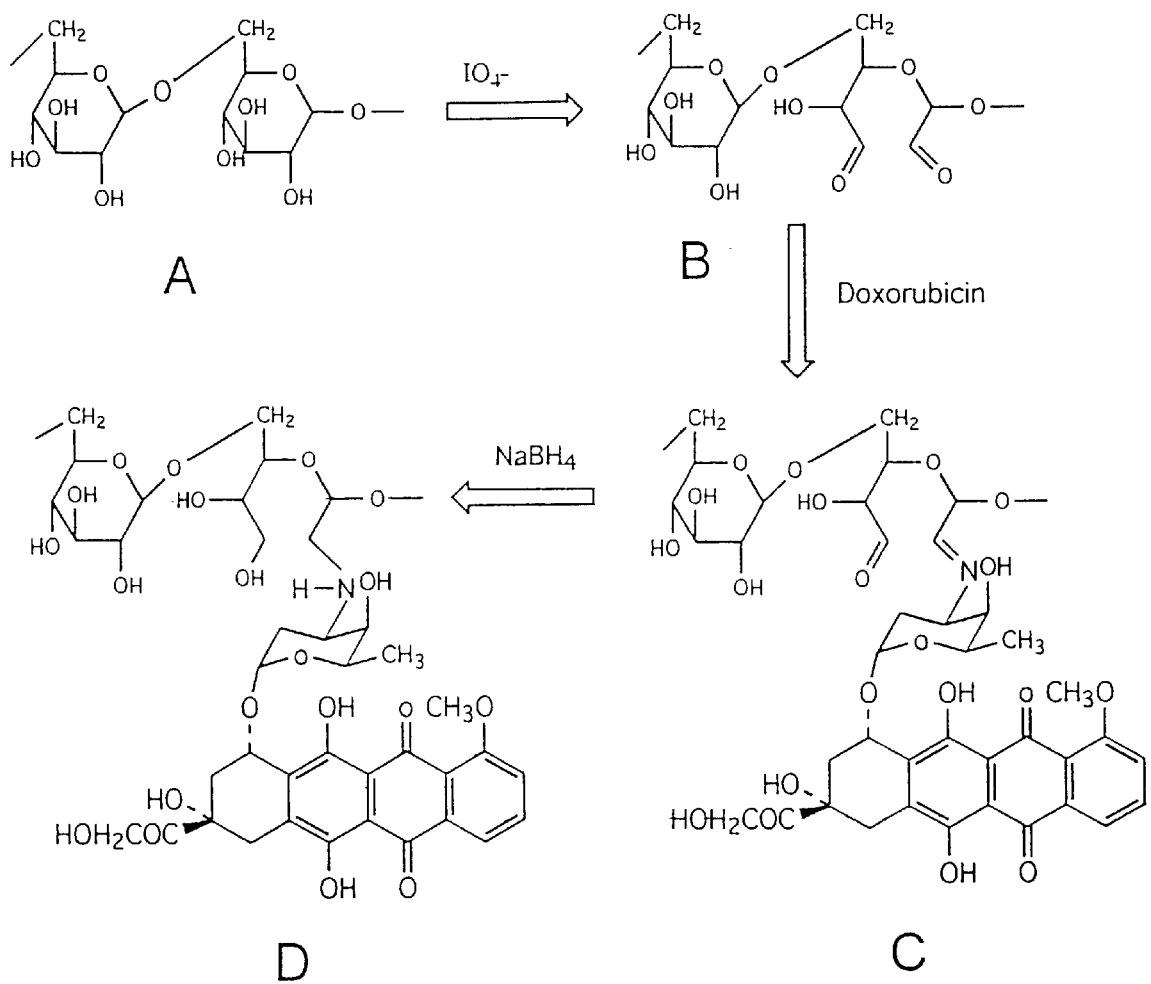
FIG. 1 illustrates the reaction scheme of one embodiment of the method of the invention.

HPLC-GPC was performed on a Bio-Sil R SEC-125 HPLC Gel Filtration Column 300×7.5 mm (Japan), using DDW as the mobile phase.

GPC was performed on a column containing a total volume of 55 ml of Sephadex G-75 and a void volume of 19 ml using DDW as an eluent.

2. Spectral Methods

UV spectra were recorded using a UVIKON Spectrophotometer (Kontron Instruments).

IR spectra were recorded using a Perkin-Elmer System 2000 FT-IR.

NMR spectra were taken by a Varian 300 MHz NMR spectrometer.

3. Sterilization and Lyophilization of Conjugates

Sterile conjugates for the animal studies were prepared by filtration through sterile pyrogen-free filters (0.2 Micron, 20 mm, 45 mm, Schleicher & Schuell, Dassel, Germany). Lyophilization was performed in a Christ Alpha-Is Lyophilizer, Germany. The sterility was validated by a sterility test using a Bactec 46 apparatus (Johnson Laboratories, Towson, Md., USA). This instrument is designed to measure radioactive carbon dioxide quantitatively in Bactec cultural vials inoculated with sample tests. The detection of $^{14}CO_2$, above a given baseline level in culturing aerobic or anaerobic vials indicates the presence of viable microorganisms in the original inoculum.

4. Preparation of Dialdehyde Dextran

Dialdehyde dextran (DAD) was prepared from the reaction of dextran with potassium periodate and purified by anion-exchange chromatography. In a typical experiment, dextran of average MW 40,000 (1 g, 0.0599 mole glucose units) was dissolved in 20.0 ml of DDW. Potassium periodate (1.275 g, 0.0554 mole) was added and the mixture was stirred at room temperature for 2 h until the potassium periodate was completely dissolved. The DAD formed was separated from excess periodate and reaction by-products by applying it to a column (6 mm×80 mm, $V_0$=2.0 ml) filled with Dowex-1 in the acetate form. Dowex-acetate was obtained by the pretreatment of the commercial anion exchanger with aqueous 1M acetic acid solution. The purified DAD at a concentration of 50.0 mg/ml exhibited a degree of oxidation in the range of 50%, as determined by the iodometric method. DADs with a 5 to 50% degree of oxidation were obtained from the reaction with a proportional amount of periodate under similar conditions. The degree of oxidation was determined by titration with hydroxyl amine. Arabinogalactan (AG) was similarly oxidized to yield dialdehyde arabinogalactan (DAAG) with 5 to 50% degree of oxidation.

5. In vitro Release (dialysis tubing method)

A solution of the Schiff base or the amine conjugates (100 mg in 5 ml phosphate buffer pH7.4) was placed into a cellulose dialysis tubing of 12,000 MW cut off and the bag was placed into a 100 ml. buffer solution at 37° C. The drug release to the solution was monitored by UV absorption at 280 nm, unless otherwise indicated.

6. Anti-cancer Cell Culture

The anti-cancer activity of the conjugates was determined in cell culture as follows: M109 cells from lung carcinoma affected mice were cultured in 90% RPMI 1640, 10% FCS native, 1% penicillin and streptomycin, 1% L-glutamine. Each experiment was performed in a 96 well plate where 16 of the outer wells were filled with 0.2 ml saline solution and used as controls. The other wells were filled with 1500–2000 cells/0.2 ml medium. After one day of incubation at which time the cells stick to the surface and behave normally, increasing concentrations of free drug or drug-conjugate in water or water-DMSO solution were added to the cell incubated wells (up to 25 μl).

The drug free solution was used as controls, and all experiments were conducted in triplicate. The plates were incubated for 72 hours in a humidified 5% $CO_2$ chamber at 37° C. Plates containing cells only were used as controls for normal cell growth. At the end of the experiment, the number of cells was determined by a colorimetric method using methylene blue and a microplate reader. The percent of survival of cells was calculated from the difference between the background reading, the initial number of cells and the number of cells remaining after incubation.

7. Anti-microbial Activity

The antimicrobial activity of the conjugates was assayed by a cup method[9] (agar plate method) using *Escherichia coli* agar plates and measuring the zone of growth inhibition.

EXAMPLES

I. Conjugation of Doxorubicin to DAD

Doxorubicin (DOX, also called adriamycin) was conjugated to oxidized dextran under various reaction conditions. In a typical experiment, 20.0 ml of purified DAD solution (25 mg/ml, Mw=19,000) was mixed with an equal volume of 0.2 M borate buffer solution pH 9.1, and 200.0 mg of DOX was added to the polymer solution (10 mg/ml). The pH value of the mixture was maintained at pH 8.9±0.1 for 16 h at 37° C. The crude conjugate was dialyzed against DDW for 30 h at 4° C. using molecular porous membrane tubing with a MW cutoff of 12,000, followed by centrifugation for 10 min at 2,000 rpm and lyophilization. The lyophilized light-yellow product (605 mg, 85% yield) contained about 20% of DOX as evaluated by UV absorption at 480 nm.

The Schiff base bonds are converted into stable amine bonds by sodium borohydride. Such an amine bond is unlikely to be easily hydrolyzed in the body. The DOX-dextran Schiff base was then dissolved in 10 ml of water containing 100 mg of $NaBH_4$ and allowed to react overnight at room temperature. The reduced conjugate was dialyzed against DDW for 30 h at 4° C. using molecular porous membrane tubing with a MW cutoff of 12,000 followed by lyophilization. The lyophilized light-yellow product was stored in a glass container protected from light and air.

II. Conjugation of DOX to Arabinogalactan (AG)

DOX was conjugated to oxidized AG under various reaction conditions. In a typical experiment, 20.0 ml of purified DAAG solution (25 mg/ml, Mw=22,000) was mixed with an equal volume of 0.2 M borate buffer solution pH 9.1, and 200.0 mg of DOX was added to the polymer solution (10 mg/ml). The pH value of the mixture was maintained at pH 8.9±0.1 for 16 h at 37° C. The crude conjugate was dialyzed against DDW for 30 h at 4° C. using molecular porous membrane tubing with MW cutoff 12,000 followed by centrifugation for 10 min at 2,000 rpm and lyophilization. The lyophilized light-yellow product (620 mg) contained about 20% by weight of DOX as evaluated by UV absorption at 480 nm. The molecular weight was MW=38,000 as determined by GPC with pollulan standards (Shodex, MW 5800–166000).

The Schiff base bonds are converted into stable amine bonds by sodium borohydride. Such an amine bond is unlikely to be easily hydrolyzed in the body. The DOX-Arabinogalactan Schiff base was then dissolved in 10 ml of water containing 100 mg of $NaBH_4$ and allowed to react overnight at room temperature. The reduced conjugate was dialyzed against DDW for 30 h at 4° C. using molecular porous membrane tubing with MW cutoff 12,000 followed by lyophilization. The lyophilized light-yellow product was stored in a glass container protected from light and air.

Figure 2B:
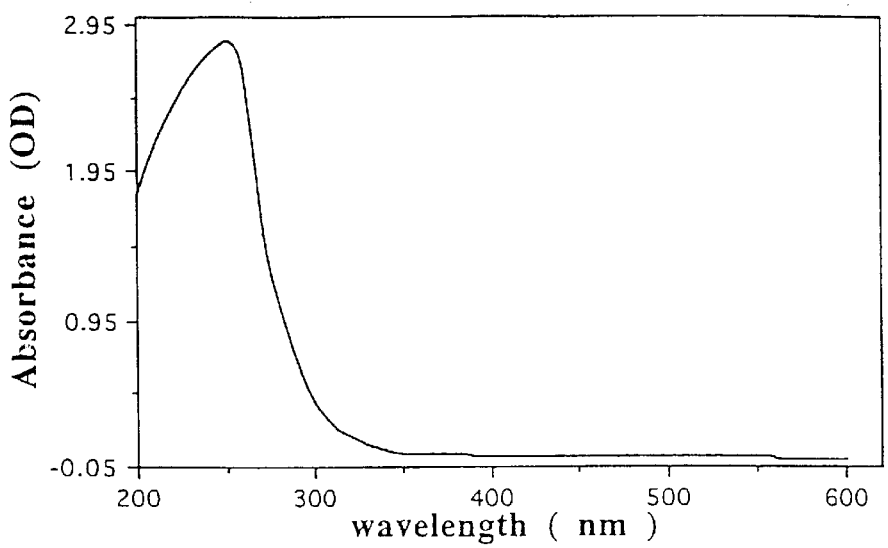
FIGS. 2a–c illustrate a UV spectra analysis of: (a) a free drug; (b) an activated polysaccharide; and (c) a conjugate product prepared according to a preferred embodiment of the method of the invention.
Figure 2A:
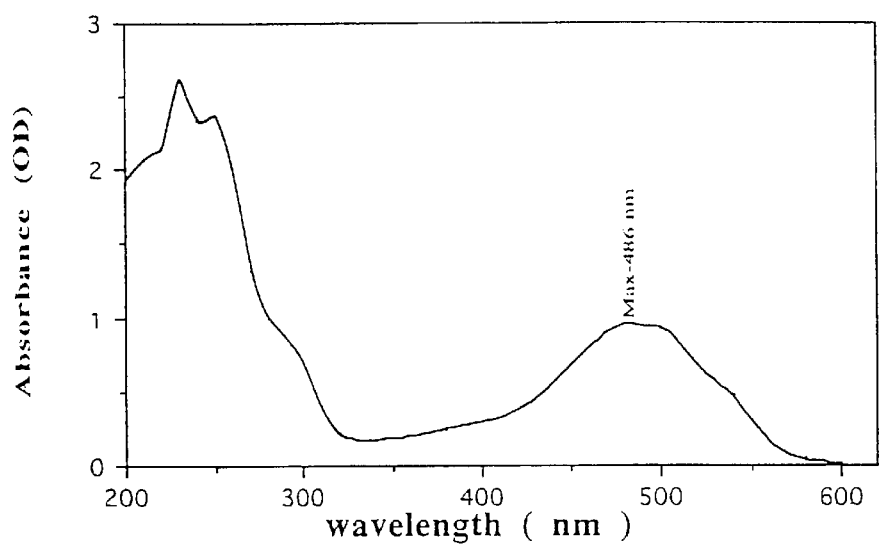
Figure 2C:
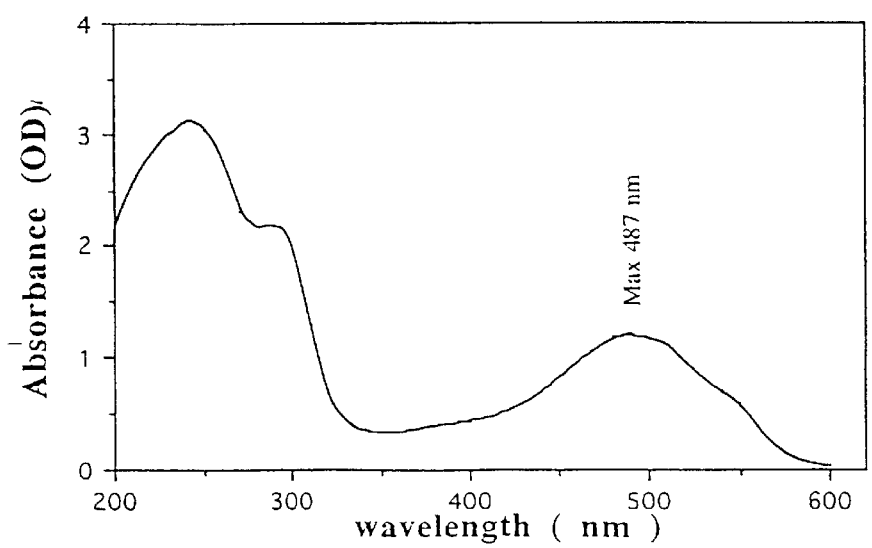

FIG. 2 illustrates the UV absorbance spectrums of the free drug in the form of an injectable composition in DDW (FIG. 2a). the dialdehyde AG in borate buffer, pH 8.9 (FIG. 2b) and the DAAG-DOX conjugate (FIG. 2c). It can be seen that the characteristic absorbance peak of DOX is substantially equivalent in the spectrums of the free drug and of the conjugate.

In vitro Release of DOX

The release of DOX from the AG conjugates was determined using dialysis tubing as described above. The DOX-AG imine conjugate, the DOX-AG amine conjugate and a solution of the native drug were studied. The amount of DOX found in the solution was 2, 5, 8, 10 and 12% of the total dose after 2, 4, 7, 12 and 32 hours, respectively. The reduced amine conjugate showed less than 1% release of the loaded dose after 3 days in the buffer solution while 90% of the free drug was released from the dialysis tube after 5 hours.

In vitro Anticancer Activity

The in vitro cell culture was conducted as described above. The imine derivative of DOX was effective to the same order of magnitude as the free drug, while the reduced derivative showed a 20% activity as compared to the free drug.

III. Conjugation of Mitomycin C to AG

One gram of AG (molecular weight of 28,000) was dissolved in 50 ml solution containing 0.3 gram of potassium periodate. The solution was mixed for 3 hours at room temperature. The solution was then passed through a Dowex column and dialyzed and lyophilized to yield a white powder free of oxidizing agent. The pure dialdehyde AG (200 mg) was dissolved in 10 ml boric acid buffer pH 8.9 and mixed with 20 mg of Mitomycin C in 5 ml of water. The solution was mixed for 24 hours, and then dialyzed with water and lyophilized to yield the Schiff base. The Schiff base conjugate was reduced with 1.1 equivalents of $NaBH_4$ for 2 hours at room temperature. The solution was purified by dialysis and lyophilized. The amount of conjugated drug was 8% by weight as determined by UV absorption at 280 nm. The molecular weight of the lyophilized product was 58,000.

In vitro Release of Mitomycin C

The Mitomycin release into the solution was measured as described above. The amount of drug found in the solution was 1, 2, 4, 5 and 8% of the total dose after 2, 4, 7, 12 and 32 hours, respectively. The reduced amine conjugate showed less than 1% of the loaded dose after 3 days in the buffer solution.

In vitro Cell Culture Activity

The anti-cancer activity of the conjugates was determined as above. Both amine and imine AG conjugates of mitomycin were as effective as the free drug and had an $IC_{50}$ (inhibition concentration for 50% survival) in the range of $10^{-7}$ molar of the drug.

In vitro Antimicrobial Activity

The antimicrobial activity of the conjugates was assayed as described above. After 24 hours of incubation the imine and amine conjugates and the free drug showed a significant inhibition zone (>10 mm).

IV. Conjugation of Polymyxin B to AG

Pure oxidized AG was prepared as described above. The pure dialdehyde AG (200 mg) was dissolved in 10 ml sodium borate buffer pH 8.9 and mixed with 20 mg of Polymyxin B in 5 ml of water. The solution was allowed to mix for 24 hours. The solution was dialyzed with water and lyophilized to yield the Schiff base. The Schiff base conjugate was reduced with 1.1 equivalents of $NaBH_4$ for 2 hours at room temperature. The solution was purified by dialysis and lyophilized. The amount of conjugated drug was determined from the nitrogen content. The MW of the imine and amine conjugates was MW=25,000.

V. Conjugation of Taxol-glycine to AG

Taxol® was esterified with glycine using DCC as coupling agent. The resulted Taxol derivative which now contained a primary amine (glycine residue) was reacted with pure oxidized AG at a 1:4 molar ratio of Taxol-glycine:aldehyde groups in the polymer sample. The reaction was carried out in a mixture of 1:9 DMSO:water solution at pH 8.5 for 8 hours at room temperature. The reaction mixture was centrifuged to remove insoluble particles and then lyophilized to yield an off-white powder.

The powder was soluble in saline nd contained about 16% by weight of Taxol as determined by H-NMR. The Schiff base was farther reduced to the more stable amine conjugate by $NaBH_4$ in water at room temperature. Di- and tri-peptide derivatives of Taxol having a free amine available for conjugation were conjugated to both AG and dextran using the above procedure. The short peptide chain can consist of the same (trialanine or triphenylalanine) or different amino acids and contain 10 amino acids or less.

VI. Conjugation of Gentamicin and Tobramicin to AG

The aminoglucoside antibiotics, gentamicin and tobramicin were conjugated to AG via a Schiff base or amine bond using a procedure similar to that described for polymyxin.

The antimicrobial activity of these conjugates was determined as described above. Saline solutions of equivalent amounts of the drug in free form or the imine or amine AG conjugates were absorbed onto a circular filter paper (6 mm in diameter) and placed on a seeded agar plate with *Staphylococcus Aureus* ($10^5$/ml) and *E. Coli* incubated for 24 hours at 37° C. All three samples showed an inhibition zone where the free drug and the imine conjugates were most effective (>10 mm), the amine conjugate was less effective (5–6 mm) for both bacteria. Similar results were obtained for the Polymyxin derivatives.

VII. Conjugation of Dexamethasone to AG

Dexamethasone, a poorly soluble antiinflammatory drug, was derivatized by esterification of the hydroxyl group with alanine derivative was reacted with pure oxidized Arabinogalactan to yield the Schiff base which then was reduced to the amine conjugate using the procedures described above. In a typical experiment, 10 mg of the dexamethasonealanine tripeptide derivative was reacted with 100 mg of oxidized AG (40% oxidation) in borate buffer solution pH 8.9 at room temperature for 24 hours. The solution was then lyophilized to yield a white material which contain dexamethasone as determined by H-NMR.

VIII. Conjugation of 5-amino Salicylic Acid to AG 5-amino salicylic acid was conjugated to oxidized AG from the reaction of 100 mg of 5-amino salicylic acid with 300 mg 40% oxidized AG (MW=22,000) in borate buffer pH 8.9 at room temperature for 24 hours. The imine derivative was obtained in good yields. The conjugate was reduced to the amine derivative using cyanoborohydride in water.

In vitro release of the conjugated drug in phosphate buffer pH 7.4 using the dialysis tubing method showed a 28% release after 24 hours at 37° C.

IX. Conjugation of Somatostatin to AG

Somatostatin was conjugated to oxidized AG via an amine or imine bond as follows: To a solution of pure oxidized AG (100 mg in 10 ml borate buffer solution pH 8.9) was added 20 mg of somatostatin and the mixture was stirred over night at 4° C. The clear solution was dialyzed through a cellulose dialysis bag of 12,000 molecular weight cut off to remove the salts and unbound drug and the solution was lyophilized to yield 115 mg of a white solid which corresponds to about 70% binding. The Schiff base was farther hydrogenated to the amine conjugate using NaBH4 as described above. The conjugation yield was confirmed by nitrogen analysis of the product.

In vitro release of Somatostatin was determined as described in the Methods and the somatostatin concentration was determined by the Folin-Lowry method for peptide analysis[10]. The amine conjugate did not release any somatostatin to the solution after 24 hours in buffer pH 7.4 at 37° C. while about 5 and 18% of the conjugated drug were released after 5 and 24 hours respectively. The released drug showed similar UV spectra to the original drug and had the same retention time by HPLC analysis (C18, acetonitrile:water 1:1, 1 ml/min, Rt=5.2 min).

X. Conjugation of Insulin to AG

Insulin was conjugated to oxidized AG (50 mg with 100 mg pure oxidized AG) using the method described above for somatostatin. The conjugation yield was about 75% as determined by nitrogen analysis and the Folin-Lowry method. The Schiff base derivative released about 25% of its drug content after 24 hours in phosphate buffer solution at 25° C. The released insulin was eluted by HPLC at the same retention time as the native drug and showed a similar UV spectrum to the starting insulin.

XI. Conjugation of Nystatin (NYS) to Dextran

In order to compare the conjugation method of the invention to that described in GB 978,170, 3 Nys-dextran conjugates were prepared: (1) Nys (10 mg/ml) was conjugated to unpurified DAD (20 mg/ml) for 20 min. at 50° C. in a strong alkaline medium of 1 M NaOH (the pH of the reaction mixture decreased from 13.5 to 12.5 over the course of the reaction; (2) Nys was conjugated to unpurified DAD for 10 hours at 37° C. in 0.1M borate buffer (pH 8.8–9.0); (3) as in (2) except that carefully purified DAD (oxidative anion content <2.5%) was used in accordance with the method of the invention.

Although both conjugates #1 and #2 dissolved rapidly in water, the solutions, as well as their extremely hygroscopic lyophilizates, contained a mixture of two main fractions as measured by GPC—a minor peak corresponding to a polymeric conjugate and a major peak corresponding to a low-molecular-weight product eluting with the total volume of the chromatographic column. In both fractions, the Nys was significantly inactivated, as evidenced by the complete disappearance of the 419 nm and 393 nm UV peaks, and the remaining antifungal activity was found not to exceed 8%.

This is in marked contrast to conjugate #3 in which the two aforementioned UV peaks were of the same magnitude as in the free drug, and only a high-molecular-weight fraction was present in the HPLC elution.

The above results clearly show that both the preliminary purification of the DAD as well as the maintenance of the pH of the reaction mixture at no higher than 9.0 are required in order to obtain a stable, active Nys-conjugate preparation.

REFERENCES

1. S. W. Shalaby, ed. Biomedical polymers-Designed to degrade systems, Carl Hanser, Munich, 1994. pp.223.
2. Larsen, C., 1990, in *Dextran Prodrugs. Physico-chemical and chemical aspects in relation to in vivo properties*, Arhus. Odense. 233p.
3. Levy-Schaffer, F., Bernstein, A., et al., 1982, *Cancer Treat. Rep.*, 66, 107–114.
4. Bernstein, A., Hurwitz, E., et al., 1978, *J. Nat. Cancer Inst.*, 60, 379–384.
5. Law, S., Lo, W., & Teh, G., 1988, *Drug. Del. Ind. Pharm.*, 14, 143–153.
6. Rogovin, Z., Vyrnik, A., Khomyakov, K. et al., Vyrnik, A. and Rogovin, Z., 1965 Vysokomol. soed., 7, 1035–1040.
7. Hurwitz, E., et. al., 1980, J. Appl. Biochem., 2, 25–35.
8. U.S. Pat. No. 4,446,316.
9. Hata, T., et al., 1956, J. Antibiot., Tokyo. 9, 141.
10. Stewart, J. M., Young, J. D., Solid Peptide Synthesis, Rockford, Ill., USA, Price Chem. Company, 1984, pp 115.

The scope of the invention is not to be construed as limited by the illustrative embodiments set forth herein, but is to be determined in accordance with the appended claims.

We claim:

1. A water-soluble conjugate of a polysaccharide and an unoxidized, oxidation-sensitive substance, said substance being conjugated to said polysaccharide via an imine bond, wherein said polysaccharide is activated as a dialdehyde and purified from interfering anions and by-products on a column filled with a strongly basic anion exchanger, with the proviso that said substance does not include polyene antibiotics.

2. A conjugate according to claim 1 wherein said substance is selected from the group consisting of amine containing low molecular weight drug and drug derivatives, and low molecular weight polypeptides and polypeptide analogs.

3. A conjugate according to claim 2 wherein said low molecular weight drugs are selected from the group consisting of 5-amino salicylic acid, aminoglucoside antibiotics, flucytosine, pyrimethamine, sulfadiazine, dapsone, trimethoprim, mitomycins, methotrexate, doxorubicin, daunorubicin and polymyxin B.

4. A conjugate according to claim 2 wherein said amine containing low molecular weight drug derivatives are oligopeptyl esters of hydroxyl containing drugs.

5. A conjugate according to claim 2 wherein said low molecular weight polypeptides contain at least one amino acid selected from the group consisting of cysteine, methionine, tyrosine, histidine and tryptophan.

6. A conjugate according to claim 5 wherein said low molecular weight polypeptide is selected from the group consisting of luteinizing hormone releasing hormone (LHRH), bradykinin, vasopressin, oxytocin, somatostatin, thyrotropin releasing factor (TRF), gonadotropin releasing hormone (GnRH), insulin and calcitonine.

7. A conjugate according to claim 2 wherein said polypeptide analogs are selected from the group consisting of cyclic derivatives, N-alkyl derivatives, derivatives in which fatty acids are attached to the amino acid terminals or along the peptide chain, and reverse amino acid derivatives of said polypeptide.

8. A conjugate according to claim 1 wherein said polysaccharide is selected from the group consisting of branched and linear polysaccharides.

9. A conjugate according to claim 8 wherein said branched polysaccharide is selected from the group consisting of arabinogalactan (AG) and branched dextran.

10. A water-soluble conjugate of a polysaccharide and an unoxidized, oxidation-sensitive substance, said substance being conjugated to said polysaccharide via an amine bond, wherein said polysaccharide is activated as a dialdehyde and purified from interfering anions and by-products on a column filled with a strongly basic anion exchanger, with the proviso that said substance does not include polyene antibiotics.

11. A conjugate according to claim 10 wherein said substance is selected from the group consisting of amine containing low molecular weight drug and drug derivatives, and low molecular weight polypeptides and polypeptide analogs.

12. A conjugate according to claim 11 wherein said low molecular weight drugs are selected from the group consisting of 5-amino salicylic acid, aminoglucoside antibiotics, flucytosine, pyrimethamine, sulfadiazine, dapsone, trimethoprim, mitomycins, methotrexate, doxorubicin, daunorubicin and polymyxin B.

13. A conjugate according to claim 11 wherein said amine containing low molecular weight drug derivatives are oligopeptyl esters of hydroxyl containing drugs.

14. A conjugate according to claim 11 wherein said low molecular weight polypeptides contain at least one amino acid selected from the group consisting of cysteine, methionine, tyrosine, histidine and tryptophan.

15. A conjugate according to claim 14 wherein said low molecular weight polypeptide is selected from the group consisting of luteinizng hormone releasing hormone (LHRH), bradykinin, vasopressin, oxytocin, somatostatin, thyrotropin releasing factor (TRF), gonadotropin releasing hormone (GnRH), insulin and calcitonine.

16. A conjugate according to claim 11 wherein said polypeptide analogs are selected from the group consisting of cyclic derivatives, N-alkyl derivatives, derivatives in which fatty acids are attached to the amino acid terminals or along the peptide chain, and reverse amino acid derivatives of said polypeptide.

17. A conjugate according to claim 10 wherein said polysaccharide in selected from the group consisting of branched and linear polysaccharides.

18. A conjugate according to claim 17 wherein said branched polysaccharide is selected from the group consisting of arabinogalactan (AG) and branched dextran.

19. A method for producing a water-soluable polysaccharide conjugate of an unoxidized, oxidation sensitive substance comprising the steps of:

(a) activating said polysaccharide to a dialdehyde by periodate oxidation;

(b) purifying said dialdehyde from interfering anions and by-products by applying it to a strongly basic anion exchanger;

(c) coupling said substance to said purified dialdehyde by Schiff base formation to form said conjugate; and (d) optionally reducing said conjugate to an amine conjugate by a reducing substance, with the proviso that said substance does not include polyene antibiotics.

20. A method according to claim 19 wherein said conjugate is purified after step (c) or optional step (d) from undesired byproducts and unreacted reactants.

21. A method according to claim 19 wherein said substance is selected from the group consisting of amine containing low molecular weight drug and drug derivatives, and low molecular weight polypeptides and polypeptide analogs.

22. A method according to claim 19 wherein said polysaccharide is selected from the group consisting of branched and linear polysaccharides.

23. A method according to claim 19 wherein said branched polysaccharide is selected from the group consisting of arabinogalactan (AG) and branched dextran.

24. A method according to claim 19 wherein said reducing substance is selected from the group consisting of $NaBH_4$ and $NaHSO_3$.

25. A water-soluble polysaccharide imine conjugate of an unoxidized, oxidation-sensitive substance prepared according to the method of claim 19.

26. A water-soluble polysaccharide amine conjugate of an unoxidized, oxidation-sensitive substance prepared according to the method of claim 19.

27. A pharmaceutical composition for use in the treatment of a physiological disorder comprising the conjugate of claim 1 together with a pharmaceutically acceptable carrier.

28. A pharmaceutical composition for use in the treatment of a physiological disorder comprising the conjugate of claim 10 together with a pharmaceutically acceptable carrier.

29. A pharmaceutical composition for use in the treatment of a physiological disorder comprising the conjugate of claim 25 together with a pharmaceutically acceptable carrier.

30. A pharmaceutical composition according to claim 27 for use in the treatment of cancer wherein said unoxidized, oxidation-sensitive substance is an anticancer agent.

31. A pharmaceutical composition according to claim 27 for use in the treatment of microbial infections wherein said unoxidation-sensitive substance is an antimicrobial agent.

32. A pharmaceutical composition according to claim 27 for use in the treatment of inflammation, wherein said unoxidized, oxidation-sensitive substance is an anti-inflammatory agent.

* * * * *